United States Patent [19]

Sakakibara

[11] 4,237,047
[45] Dec. 2, 1980

[54] PEPTIDE DERIVATIVE

[75] Inventor: Shumpei Sakakibara, Suita, Japan

[73] Assignee: Ajinomoto Company, Incorporated, Tokyo, Japan

[21] Appl. No.: 61,422

[22] Filed: Jul. 27, 1979

[30] Foreign Application Priority Data

Aug. 10, 1978 [JP] Japan .................................. 53-97579

[51] Int. Cl.³ .................. C07C 103/52; C07D 311/06
[52] U.S. Cl. ......................... 260/112.5 R; 260/343.45
[58] Field of Search ...................... 260/112.5 R, 343.45

[56] References Cited

U.S. PATENT DOCUMENTS 4,147,692  4/1979  Nagatsu et al. ............... 260/112.5 R

OTHER PUBLICATIONS

Takashi, M., et al., J. Biochem., 82, 1495-1498 (1977).

Primary Examiner—Delbert R. Phillips

Attorney, Agent, or Firm—Oblon, Fisher, Spivak, McClelland & Maier

[57] ABSTRACT

A peptide derivative having the formula:

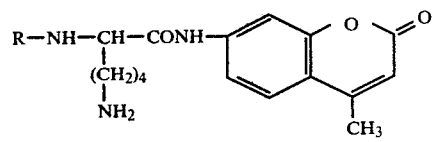

wherein R is a radical selected from the group consisting of hydrogen, glutamyl, isoleucyl-glutamyl, phenylalanyl-glutamyl, lysyl, glutamyl-lysyl, phenylalanyl-glutamyl-lysyl, leucyl, and valyl-leucyl. This compound is useful as a fluorescent substrate for the sensitive determination of enzymatic activity.

6 Claims, No Drawings

PEPTIDE DERIVATIVE

BACKGROUND OF THE INVENTION

1. Field of the Invention

The present invention relates to a novel peptide derivative useful as fluorescent substrate for measuring the activity of specific enzymes, or an intermediate product thereof, and more particularly, to 7-($N^\alpha$-substituted or non-substituted lysyl)amino -4-methylcoumarin.

SUMMARY OF THE INVENTION

As a result of preseverant efforts towards obtaining a substrate whereby activity of specific enzymes can be measured in a simple and highly sensitive way, inventor has succeeded in synthesizing a peptide derivative shown by a general formula

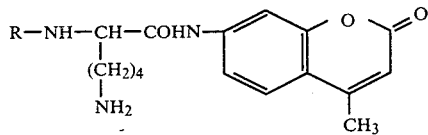

and discovered that the novel peptide derivative may be used as a fluorescent substrate, or its intermediate product, for an enzyme such as trypsin or plasmin, the activity of which can be measured in a simple and highly sensitive way.

DESCRIPTION OF THE PREFERRED EMBODIMENTS

R designates hydrogen atom or glutamyl, isoleucyl-glutamyl, phenylalanyl-glutamyl, lysyl, glutamyl-lysyl, phenylalanyl-glutamyl-lysyl, leucyl, or valyl-leucyl group. In the peptide derivative of the above general formula, the $N^\alpha$-amino group may be protected by customarily employed protective groups for the $N^\alpha$-amino group of peptides such as acyl groups such as acetyl or benzoyl, carbobenzoxy group, tert-alkyloxycarbonyl group, tosyl group or glutaryl group, while at least one of the $N^\epsilon$-amino group may be protected by customarily employed protective groups for $N^\epsilon$-amino group, such as acyl group, carbobenzoxy group, or tert-alkyloxycarbonyl group.

In cases where the peptide derivative of the above general formula comprises glutamyl group, carboxyl group may be protected by protective groups for the carboxyl groups as customarily employed in peptide synthesis such as esterification with alcohols such as benzyl alcohol, or alkali salt formation.

The peptide derivative may be in the form of acid salts of, for exmaple acetic acid or hydrochloric acid, or in the form of hydrates.

The above peptide derivative is 7-(lysyl)-amino-4-methyl-coumarin if R is hydrogen atom; 7-(glutamyl-lysyl)-amino-4-methylcoumarin if R is glutamyl group; 7-(isoleucyl-glutamyl-lysyl)-amino-4-methylcoumarin if R is isoleucyl-glutamyl group; 7-(phenylalanyl-glutamyl-lysyl)-amino-4-methylcoumarin if R is phenylalanyl-glutamyl group; 7-(glutamyl-lysyl-lysyl)-amino-4-methylcoumarin if R is glutamyl-lysyl group; 7-(phenylalanyl-glutamyl-lysyl-lysyl)-amino-4-methylcoumarin if R is phenylalanyl-glutamyl-lysyl group; 7-(leucyl-lysyl)-amino-4-methylcoumarin if R is leucyl group; and 7-(valyl-leucyl-lysyl)-amino-4-methylcoumarin if R is valyl-leucyl group.

The peptide derivative of the present invention can be synthesized in a following way.

7-amino-4-methylcoumarin and lysine, two amino groups of which are protected, are reacted together in the presence of condensing agents such as dicyclohexylcarbodiimide (DCCD) congentionally employed for peptide synthesis. Next, the protective groups for the amino groups are removed in a manner as conventionally used in peptide synthesis for providing 7-lysyl-amino-4-methylcoumarin.

The peptide derivative of the present invention can be prepared by the use of the thus obtained 7-($N^\alpha$-protective-$N^\epsilon$-protective-lysyl)-amino-4-methylcoumarin as a starting material and by using a conventional manner employed in peptide synthesis. For example, by reacting glutamic acid of which the amino group and $\gamma$-carboxyl group are protected, with the above methylcoumarin derivative in which $N^\alpha$ is not protected in the presence of said condensing agent, or by reacting an active ester of glutamic acid as above mentioned and the above methylcoumarin derivative, and removing the protective groups, 7-($N^\alpha$-glutamyl-lysyl)-amino-4-methylcoumarin can be obtained. By reacting 7-($N^\alpha$-nonprotective-$\gamma$-protective-glutamyl-$N^\epsilon$-protective-lysyl)-amino-4-methylcoumarin further with an active ester of isoleucine having protected amino group, then by removing the protective groups, 7-(isoleucyl-glutamyl-lysyl)-amino-4-methylcoumarin is obtained. If an active ester of phenylalanine having protected amino group is used in the above reaction instead of the active ester of amino-group-protected isoleucine and the protective groups are removed in the similar way, 7-(phenylalanyl-glutamyl-lysyl)-amino-4-methylcoumarin is obtained.

Also, by reacting 7-($N^\alpha$-nonprotective-$N^\epsilon$-protective-lysyl)amino-4-methylcoumarin with an active ester of amino-group-protected leucine and by removing the protective groups in the similar way, 7-(leucyl-lysyl)-amino-4-methylcoumarin is obtained.

Further, by reacting 7-($N^\alpha$-nonprotective-leucyl-$N^\epsilon$-protective-lysyl)-amino-4-methylcoumarin and an active ester of amino-group-protected valine and removing the protective groups in the similar way, 7-(valyl-leucyl-lysyl)-amino-4-methyl-coumarin is obtained.

By reacting 7-($N^\alpha$-nonprotective-$N^\epsilon$-protective-lysyl)-amino-4-methylcoumarin with an active ester of $\alpha,\epsilon$-diprotected lysine and removing the protective groups, 7-(lysyl-lysyl)-amino-4-methylcoumarin is obtained.

By reactiing 7-($N^\alpha$-nonprotective-$N^\epsilon$-protective-lysyl-N-$\epsilon$-protective-lysyl)-amino-4-methylcoumarin with an active ester of glutamic acid with protected-$\gamma$-carboxyl group and removing the protective groups, 7-(glutamyl-lysyl)-amino-4-methylcoumarin is obtained.

By reacting 7-($N^\alpha$-nonprotective-$\gamma$-protective-glutamyl-$N^\epsilon$-protective-lysyl-$N^\epsilon$-protective-lysyl)-amino-4-methylcoumarin with an active ester of amino-group-protected phenylalanine and removing the protective group in the similar way, 7-(phenylalanyl-glutamyl-lysyl-lysyl)-amino-4-methylcoumarin is obtained.

If a peptide derivative has active groups ($N^\epsilon$-amino group or $\gamma$-carboxylyl group) in addition to $N^\alpha$-amino group of the terminal amino acid and, among these active groups, only the $N^\alpha$-amino group of the terminal amino acid is to be protected, the peptide derivative in which the active groups other than the $N^\alpha$-amino group of the terminal amino acid are protected may be subjected to a suitable removing process such as hydrogenation in a palladium-carbon catalyst, depending upon the kinds of the protective groups. Thus, if th $N^\alpha$-protective group is tert-alkyloxycarbonyl group and the other protective groups are carbobenzoxy group or benzylester, the protective groups of the active groups other than the $N^\alpha$-amino group of the terminal amino acid can be selectively removed by such hydrogenation.

The condensation reaction for the synthesis of the peptide derivative of the present invention should preferably be conducted in a suitable solvent such as dimethylformamide (DMF), dimethylsulfoxide, water or mixtures thereof. The carboxyl component to be reacted with an amino component should preferably be employed in the form of an active ester which may preferably be N-hydroxysuccinimide ester or p-nitrophenylester. While the reaction using this active ester proceeds sufficiently at room temperature, it may also be promoted by heating as the occasion may demand.

After completion of reaction, the reaction mixture is concentrated and dried to a solid substance and the residue is refined by gel chromatography and freeze-dried.

If the resulting compound has protective groups for an amino or carboxilic group, these protective groups may be removed by employing a conventional removing process for the protective groups. For example, carbobenzoxy groups or benzyl esters can be removed by hydrogenation in alcohol or similar solvents, while tert-butyloxycarbonyl group can be removed by reacting the same with toluensulfonic acid for about 90 minutes in acetic acid or other solvents.

The peptide derivative of the present invention in an isolated form may be converted into an acid salt, or the peptide derivative in the form of an acid salt may be converted into an isolated form, as the occasion may demand. Examples of such acid salts are inorganic acid salts such as hydrochloride, sulfate, nitrate or phosphate and organic acid salts such as acetate, oxalate, tartarate, succinate, citrate or toluensulfonate.

The peptide derivative thus obtained were identified by elementary analysis, amino acid analysis, UV absorption spectrum, and by UV absorption spectrum for the peptide derivative hydrolyzed with trypsin in comparison with the spectrum for 7-amino-4-methylcoumarin.

As the compounds of the present invention may be hydrolyzed by enzymes such as trypsin, plasmin and the like, the compounds are highly suitable as synthetic substrates for these specific enzymes.

The amino acid comprises in the peptide derivative of the present invention may be in the L- or D- form, however, the L-form is more preferred because the D-form amino acid at the terminal of the carboxy group is not hydrolyzed by enzymes.

The present invention will be further described by referring to several examples.

EXAMPLE 1

19 g (0.05 mol) of $N^\alpha$-t-butyloxycarbonyl-$N^\epsilon$-carbobenzoxy-L-lysine and 8.7 g (0.05 mol) of 7-amino-4-methylcoumarin were dissolved in 80 ml of DMF. To the resulting mixture were added 11 g (0.053 mol) of DCCD in a glacial bath. The resulting product was stirred for 15 hours at 20° C. and dicyclohexylurea thus prepared was filtered off while the filtrate was concentrated. To the remaining product was added 100 ml of 0.5 N hydrochloric acid and an oily substance thus produced was extracted with 200 ml of ethyl acetate. An organic phase was washed twice with 100 ml of 0.5 N hydrochloric acid, twice with 100 ml of 5% aqueous solution of sodium bicarbonate and with 100 ml of water, dried over magnesium sulfate, and concentrated to obtain a solid substance. 200 ml of ether was added to the remaining product which was thus triturated and recovered by filtration. The resulting product was dissolved in 150 ml of methyl alcohol, decolored with activated carbon and added with 0.1 N hydrochloric acid and the resulting solid substance was recovered by filtration. The product was washed with 200 ml of water to 7-($N^\alpha$-t-butyloxycarbonyl-$N^\epsilon$-carbobenzoxy-L-lysyl)-amino-4-methylcoumarin hemihydrate. Yield was 9.8 g (36%); melting point was 125° to 127° C.; and specific rotation was $[\alpha]_D^{27} = -8.0°$ (C=2.96. DMF).

Elementary analysis: Found.. C63.85%, H6.56%, N8.24%. Calculated as $C_{29}H_{35}O_7N_3 \cdot \frac{1}{2} H_2O$ : C63.72%; H6.64%; N7.70%.

EXAMPLE 2

To 2.7 g (5 milli mol) of 7-($N^\alpha$-t-butyloxycarbonyl-$N^\epsilon$-carbobenzoxy-L-lysyl)-amino-4-methylcoumarin were added 5 ml of acetic acid and then 1.15 g (6 milli mol) of toluenesulfonic acid monohydrate. The resulting mixture was stirred at 25° C. for 60 min and added with 200 ml of ethyl acetate and the resulting solid substance was recovered by filtration. The latter was dissolved in 10 ml of DMF, neutralized with 0.7 ml of triethylamine, added with 3.0 g (6.9 milli mol) of t-butylcarbonyl-$\gamma$-benzyl-L-glutamyl-N-hydroxysuccinimide ester, and the mixture thus obtained was stirred at 25° C. for 20 hours.

100 ml of a 5% aqueous solution of sodium bicarbonate was added to the resulting mixture and an oily substance thus produced was extracted with 100 ml of ethyl acetate.

An organic layer was washed twice with 100 ml of a 5% aqueous solution of sodium bicarbonate and twice with 100 ml of 0.5 N hydrochloric acid then with 100 ml of water, dried over magnesium sulfate, concentrated, and dried to a solid substance. To the remaining product were added 20 ml of ethyl acetate and 200 ml of ethyl ether and a resulting gel-like solid substance was recovered by filtration and washed with 100 ml of ethylether to 7-($N^\alpha$-t-butyloxycarbonyl-$\gamma$-benzyl-L-glutamyl-$N^\epsilon$-carbobenzoxy-L-lysyl)-amino-4-methylcoumarin monohydrate. Yield: 2.7 g, melting point: 112° to 118° C., specific rotation: $[\alpha]_D^{27} = -0.2°$ (C=1.53, DMF).

Elementary analysis: Found.. C 63.61%, H 6.41%, N 7.76% Calculated as $C_{41}H_{48}O_{10}N_4 \cdot H_2O$: C 63.55%, H 6.50%, N 7.23%.

EXAMPLE 3

To 0.73 g (1 milli mol) of 7-($N^\alpha$-t-butyloxycarbonyl-$\gamma$-benzyl-L-glutamyl-$N^\epsilon$-carbobenzoxy-L-lysyl)-amino-4-methylcoumarin were added 2.5 ml of acetic acid and then 0.23 g (1.2 milli mol) of toluene-sulfonic acid monohydrate. The resulting mixture was stirred at 20° C. for 3 hours and added with 50 ml of ethyl acetate. The resulting solid substance was recovered by filtration and washed with 20 ml of ethyl acetate.

The solid substance thus washed was dissolved in 5 ml of DMF, neutralized with 0.14 ml of triethylamine and added with 0.54 g (1.5 milli mol) of t-butyloxycarbonyl-L-phenylalanine-N-hydroxy-succinimide ester and the resulting product was stirred at 20° C. for 20 hours.

To the resulting product was added 100 ml of a 5% aqueous solution of sodium bicarbonate, and an oily substance thus obtained was extracted with 100 ml of ethyl acetate.

An organic layer was then washed twice with 100 ml of a 5% aqueous solution of sodium bicarbonate, twice with 100 ml of 0.5 N hydrochloric acid and then 100 ml of water, in this order, then dried over magnesium sulfate, concentrated and dried to a solid substance. To the remaining product was added 200 ml of ethyl ether and the resulting mixture was allowed to reflux for 30 min. After the remaining substance undissolved on heating was filtered off, the mixture was washed with 50 ml of ethyl ether to 7-($N^\alpha$-t-butyloxycarbonyl-L-phenylalanyl-$\gamma$-benzyl-L-glutamyl-$N^\epsilon$-carbobenzoxy-L-lysyl)-amino-4-methylcoumarin monohydrate. Yield: 755 mg (83%); melting point: 181° to 183° C.; specific rotation $[\alpha]_D^{27} = -7.5°$ (C=1.46, DMF).

Elementary analysis: Found: C 65.32%; H 6.40%; N 7.54%. Calculated as $C_{50}H_{57}O_{11}N_5 \cdot H_2O$, C 65.13%; H 6.45%; N 7.60%.

EXAMPLE 4

To 0.73 g (1 milli mol) of 7-($N^\alpha$-t-butyloxycarbonyl-$\gamma$-benzyl-L-glutamyl-$N^\epsilon$-carbobenzoxy-L-Lysyl)-amino-4-methylcoumarin were added 2.5 ml of acetic acid and then 0.23 g (1.2 milli mol) of toluenesulfonic acid mono hydrate and the mixture was stirred at 20° C. for 3 hours and added with 50 ml of ethyl acetate. The resulting solid substance was recovered by filtration and washed with 20 ml of ethyl acetate. This solid substance was dissolved in 5 ml of DMF, neutralized with 0.14 ml of triethylamine, added with 0.49 g (1.5 milli mol) of t-butyloxycarbonyl-L-isoleucine-N-hydroxysuccinimide ester, and stirred at 20° C. for 20 hours. To the resulting product was added 100 ml of a 5% aqueous solution of sodium bicarbonate, and an oily substance thus yielded was extracted with 100 ml of ethyl acetate.

An organic layer was then washed twice with 100 ml of a 5% aqueous solution of sodium bicarbonate, twice with 0.5 N hydrochloric acid and then with 100 ml of water, and thus an insoluble matter was produced. The insoluble matter was increased in quantity by addition of 200 ml of ether and filtered off. The remaining product was washed with 50 ml of ether to 7-($N^\alpha$-t-butyloxycarbonyl-L-isoleucyl-$\gamma$-benzyl-L-glutamyl-$N^\epsilon$-carbobenzoxy-L-lysyl)-amino-4-methylcoumarin.5/4 hydrate.

Yield: 685 mg (78%); melting point, 194° to 196° C.; specific rotation $[\alpha]_D^{27} = -6.5°$ (C=0.85, DMF).

Elementary analysis: Found: C 63.39%; H 6.95%; N 7.84%. Calculated as $C_{47}H_{59}O_{11}N_5 \cdot 5/4 H_2O$, C 63.25%; H 6.95%; N 7.85%.

EXAMPLE 5

To 0.54 g (1 milli mol) of 7-($N^\alpha$-t-butyloxycarbonyl-$N^\epsilon$-carbobenzoxy-L-lysyl)-amino-4-methylcoumarin were added 2.5 ml of acetic acid and then 0.57 g (3 milli mol) of toluenesulfonic acid monohydrate. The resulting product was stirred at 20° C. for 1 hour and added with 50 ml of ethyl acetate and a solid substance thus yielded was recovered by filtration.

This solid substance was dissolved in 10 ml of chloroform, neutralized with 0.14 ml of triethylamine, added with 0.39 g (1.2 milli mol) of t-butyloxycarbonyl-L-leucine-N-hydroxy-succinimide ester, and stirred at 20° C. for 20 hours. With the solvent distilled off, the remaining product was added with 30 ml of 5% aqueous solution of sodium bicarbonate, and an oily substance so yielded was extracted with 30 ml of ethyl acetate.

An organic layer was washed with 30 ml of a 5% aqueous solution of sodium bicarbonate, 30 ml of 0.5 N hydrochloric acid and 30 ml of water, dried over magnesium sulfate, concentrated and dried to a solid substance.

100 ml of ethyl ether was added to a remaining product and a solid substance so yielded was recovered by filtration and washed with 50 ml of ethyl ether to 7-($N^\alpha$-t-butyloxycarbonyl-L-leucyl-$N^\epsilon$-carbobenzoxy-L-lysyl)-amino-4-methylcoumarin ¼ hydrate.

Yield: 300 mg (46%); melting point, 163° to 165° C.; specific rotation, $[\alpha]_D^{27} = -9.3°$ (DMF)

Elementary analysis: Found: C 64.21%; H 7.07%; N 8.60%. Calculated as $C_{35}H_{46}O_8N_4 \cdot 1/4 H_2O$: C 64.15%; H 7.15%; N 8.55%.

EXAMPLE 6

To 217 mg (0.33 milli mol) of 7-($N^\alpha$-t-butyloxycarbonyl-L-leucyl-$N^\epsilon$-carbobenzoxy-L-lysyl)-amino-4-methylcoumarin were added 5 ml of acetic acid and then 191 mg (1 milli mol) of toluensulfonic acid monohydrate and the mixture was stirred at 20° C. for 2 hours. Acetic acid was then distilled off. 20 ml of ethyl ether was added to the remaining product and the solid substance thus yielded was recovered by filtration and washed with 10 ml of ethyl ether. The solid substance was dissolved in 10 ml of chloroform, neutralized with 0.05 ml of triethylamine, added with 126 mg (0.4 milli mol) of t-butyloxycarbonyl-L-valine-N-hydroxysuccinimide ester and stirred at 20° C. for 20 hours. The resulting product was concentrated to a solid substance. The remaining product was added with 20 ml of water, and the soluble substance was removed. The remaining product was dissolved in 10 ml of ethyl acetate and added with n-hexane to give a gel-like substance which was then recovered by filtration and washed with 20 ml of ethyl ether to 7-($N^\alpha$-t-butyloxycarbonyl-L-valyl-L-leucyl-N-carbobenzoxy-L-lysyl-amino-4-methylcoumarin.½ hydrate.

Yield: 240 mg (96%); melting point, 199° to 200° C.; specific rotation, $[\alpha]_D^{27} = -17.8°$ (C=1.15, DMF).

Elementary analysis: Found: C 63.52%; H 7.29%; N 9.27%. Calculated as $C_{40}H_{55}O_9N_5 \cdot ½ H_2O$: C 63.30%; H 7.43%; N 9.20%.

EXAMPLE 7

To 1.61 g (3 milli mol) of 7-($N^\alpha$-t-butyloxycarbonyl-$N^\epsilon$-carbobenzoxy-L-lysyl)-amino-4-methylcoumarin were added 7.5 ml of acetic acid and then 1.7 g (9 milli mol) of toluenesulfonic acid monohydrate and the resulting mixture was stirred at 20° C. for 1 hour. A solid substance thus produced was recovered by filtration. This solid substance was dissolved in 30 ml of chloroform, neutralized with 0.42 ml (3 milli mol) of triethylamine and added with 1.72 g (3.6 milli mol) of $N^\alpha$-t-butyloxycarbonyl-$N^\epsilon$-carbobenzoxy-L-lysine-N-hydroxysuccinimide ester, and the resulting mixture was stirred at 20° C. for 20 hours.

The solvent was distilled off and an oily substance yielded upon addition of 100 ml of a 5% aqueous solution of sodium bicarbonate was extracted with 100 ml of ethyl acetate. An organic layer was then washed twice with 100 ml of a 5% aqueous solution of sodium bicarbonate, twice with 100 ml of 0.5 N hydrochloric acid and 100 ml of water, in this order, dried over magnesium sulfate, then concentrated and dried to a solid substance.

200 ml of ethyl ether was added to a remaining product and a solid substance thus yielded was recovered by filtration and washed with 100 ml of ethyl ether to 7-($N^\alpha$-t-butyloxycarbonyl-$N^\epsilon$-carbobenzoxy-L-lysyl-$N^\epsilon$-carbobenzoxy-L-lysyl)-amino-4-methylcoumarin.¼ hydrate.

Yield: 1.25 g (52%); melting point, 95° to 100° C.; specific rotation $[\alpha]_D^{27} = -2.6°$ (C=1.68, DMF).

Elementary analysis: Found C 64.23% H 6.68%; N 8.59%. Calculated as $C_{45}H_{53}O_{10}N_5 \cdot ¼ H_2O$: C 64.20%; H 6.70%; N 8.70%.

EXAMPLE 8

To 1.20 g (1.5 milli mol) of 7-($N^\alpha$-t-butyloxycarbonyl-$N^\epsilon$-carbobenzoxy-L-lysyl-$N^\epsilon$-carbobenzoxy-L-lysyl)-amino-4-methylcoumarin were added 10 ml of acetic acid and then 860 mg (4.5 milli mol) of toluenesulfonic acid monohydrate and the resulting mixture was stirred at 20° C. for 2 hours. Acetic acid was then removed and a solid substance yielded upon addition of 100 ml of ethyl ether was recovered by filtration and washed with 50 ml of ethyl ether. The solid substance thus washed was dissolved in 50 ml of chloroform, neutralized with 0.21 ml (1.5 milli mol) of triethylamine and added with 823 mg (1.8 milli mol) of t-butyloxycarbonyl-γ-benzyl-L-glutamyl-p-nitrophenylesth and the resulting mixture was stirred at 20° C. for 20 hours. The solvent was distilled off, and 100 ml of ethyl ether was added to a remaining material for removal of soluble matter.

The residual substance was crystallized by addition of 100 ml of water. The crystals were recovered by filtration, washed with 20 ml of water, and then washed with 30 ml of ethyl ether to 7-($N^\alpha$-t-butyloxycarbonyl-γ-benzyl-L-glutamyl-$N^\epsilon$-carbobenzoxy-L-lysyl-$N^\epsilon$-carbobenzoxy-L-lysyl)-amino-4-methylcoumarin.

Yield: 1.45 g (95%); melting point, 160° to 162° C.; specific rotation $[\alpha]_D^{27} = -4.6°$ (C=1.23, DMF)

Elementary analysis: Found: C 64.54%; H 6.47%; N 8.14%. Calculated as $C_{55}H_{66}O_{13}N_6$: C 64.81%; H 6.53%; N 8.25%.

EXAMPLE 9

To 1.02 g (1 milli mol) of 7-($N^\alpha$-t-butyloxycarbonyl-γ-benzyl-L-glutamyl-$N^\epsilon$-carbobenzoxy-L-lysyl-$N^\epsilon$-carbobenzoxy-L-lysyl)-amino-4-methylcoumarin were added 5 ml of acetic acid and 573 mg (3 milli mol) of toluene sulfonic acid monohydrate, and the resulting mixture was stirred at 20° C. for 2 hours. Acetic acid was then distilled off and a solid substance that yielded upon addition of 100 ml of ethyl ether was recovered by filtration. This solid substance was dissolved in 5 ml of DMF, neutralized with 0.14 ml of triethylamine and added with 435 mg (1.2 milli mol) of t-butyloxycarbonyl-L-phenylalanine-N-hydroxysuccinimide ester and the resulting mixture was stirred at 20° C. for 20 hours.

The resulting product was concentrated and dried to a solid substance to which was added 100 ml of ethyl ether for removal of soluble matter. 100 ml of water was added to the remaining product which was then recovered by filtration as crystals. These crystals were then washed with 30 ml of water and 50 ml of ethyl ether to 7-($N^\alpha$-t-butyloxycarbonyl-L-phenylalanyl-γ-benzyl-L-gluatmyl-$N^\epsilon$-carbobenzozy-L-lysyl-$N^\epsilon$-carbobenzoxy-L-lysyl)-amino-4-methylcoumarin.

Yield: 1.03 g (88%); melting point, 165° to 168° C.; specific rotation $[\alpha]_D^{27} = -8.4°$ (C=1.72, DMF)

Elementary analysis: Found: C 65.72%; H 6.40%; N 8.20%. Calculated as $C_{64}H_{75}O_{14}N_7$: C 65.90%; H 6.48%; N 8.41%.

EXAMPLE 10

757 mg (1 milli mol) of 7-($N^\alpha$-t-butyloxycarbonyl-γ-benzyl-L-glutamyl-$N^\epsilon$-carbobenzoxy-L-lysyl)-amino-4-methylcoumarin was dissolved in 20 ml of methyl alcohol, 5 ml of acetic acid and 5 ml of water and added with 80 mg of a 5% palladium-carbon catalyst. The resulting mixture was stirred for 3 hours at room temperature and atmospheric pressure under circulation of hydrogen. The catalyst was then filtered off and the filtrate was concentrated and dried to a solid substance.

50 ml of ethyl ether was added to the remaining product and the solid substance thus produced was recovered by filtration and washed with 10 ml of ethyl ether to 7-($N^\alpha$-t-butyloxycarbonyl-L-glutamyl-L-lysyl)-amino-4-methylcoumarin.

Yield: 500 mg (73%); melting point, 140 C (decomposition); specific rotation $[\alpha]_D^{27} = -58.8°$ (C=3.12, $H_2O$)

Elementary analysis: Found: C 52.25%; H 6.75%; N 8.57%. Calculated as $C_{26}H_{36}N_4O_8 \cdot 2CH_3COOH \cdot 2H_2O$: C 52.31%; H 7.02%; N 8.14%.

EXAMPLE 11

633 mg (0.7 milli mol) of 7-($N^\alpha$-t-butyloxycarbonyl-L-phenylalanyl-γ-benzyl-L-glutamyl-$N^\epsilon$-carbobenzoxy-L-lysyl)-amino-4-methylcoumarin was dissolved in 20 ml of methyl alcohol, 5 ml of acetic acid and 5 ml of water and added with 60 mg of a 5% palladium-carbon catalyst. The resulting mixture was stirred for 3 hours at room temperature and atmospheric pressure under circulation of hydrogen. The catalyst was then filtered off and the filtrate was then concentrated and dried to a solid substance. The remaining substance was subjected to silica gel column chromatography (solvent system, chloroform: methyl alcohol: acetic acid=85:15:5 and 85:30:5, column size 1.5 cm by 1.5 cm) for refining and concentration of the main fractions. The remaining product was dissolved by addition thereto of 15 ml of acetic acid and freeze-dried to 7-($N^\alpha$-t-butyloxycarbonyl-L-phenylalanyl-L-glutamyl-L-lysyl)-amino-4-methylcoumarin.

Yield, 355 mg (58%); melting point, 160° C. (decomposition); specific rotation $[\alpha]_D^{27} = -41.6°$ (C=0.385, 50% DMF).

Elementary analysis: Found, C 55.87%; H 6.48%; N 7.90%. Calculated as $C_{35}H_{45}N_5O_9 \cdot 3CH_3COOH \cdot H_2O$, C 55.83%; H 6.74%; N 7.94%.

EXAMPLE 12

609 mg (0.7 milli mol) of 7-($N^\alpha$-t-butyloxycarbonyl-L-isoleucyl-γ-benzyl-L-glutamyl-$N^\epsilon$-carbobenzoxy-L-lysyl)-amino-4-methylcoumarin was dissolved in 20 ml of methyl alcohol, 5 ml of acetic acid and 5 ml of water, and added with 60 mg of a 5% palladium-carbon catalyst. The resulting mixture was stirred at room temperature and atmospheric pressure under circulation of hydrogen. The catalyst was then filtered off and the filtrate was concentrated and dried to a solid substance.

The remaining substance was subjected to silica gel chromatography (solvent system, chloroform: methyl alcohol: acetic acid=85:15:5 and 85:30:5, column size 1.5 cm by 1 5 cm) for refining and the main fractions were concentrated and dried to a solid substance. The remaining substance was dissolved by addition thereto of 15 ml of acetic acid and freeze dried to 7-(N$^\alpha$-t-butyloxycarbonyl-L-isoleucyl-L-glutamyl-L-lysyl)-amino-4-methylcoumarin. Yield: 350 mg (62%); melting point, 145° C. (decomposition); specific rotation $[\alpha]_D^{27} = -47.2°$ (C=0.305, 50% DMF).

Elementary analysis: Found.. C 53.70%; H 7.13%; N 8.50%. Calculated as $C_{32}H_{47}N_5O_9 \cdot 2 CH_3COOH \cdot 2H_2O$: C 53.92%; H 7.42%; N 8.74%.

EXAMPLE 13

150 mg (0.2 milli mol) of 7-(N$^\alpha$-t-butyloxycarbonyl-L-valyl-L-leucyl-N$^\epsilon$-carbobenzoxy-L-lysyl)-amino-4-methylcoumarin was dissolved in 10 ml of methyl alcohol, 5 ml of acetic acid and 1 ml of water, and added with 20 mg of a 5% palladium-carbon catalyst. The resulting mixture was stirred for 3 hours at room temperature and atmospheric pressure under circulation of hydrogen. The catalyst was then removed and the filtrate was concentrated to a solid substance.

The remaining substance was subjected to silica gel chromatography (solvent system, chloroform: methyl alcohol: acetic acid =85:5:5 and 85:15:5, column size 1.5 cm by 15 cm) for refining and the main fractions were collected and subjected to concentration to a solid substance. The resulting product was dissolved in 10 ml of acetic acid and freeze dried to 7-(N$^\alpha$-t- butyloxycarbonyl-L-valyl-L-leucyl-L-lysyl)-amino-4-methylcoumarin.

Yield: 100 mg (65%); melting point, 160° C. (decomposition); specific rotation $[\alpha]_D^{27} = -79.6°$ (C=1.03, H$_2$O).

Elementary analysis: Found: C 55.86%; H 7.41%; N 9.37%. Calculated as $C_{32}H_{49}N_5O_7 \cdot 2CH COOH \cdot 2 H_2O$: C 55.01%; H 7.97%; N 9.08%.

EXAMPLE 14

204 mg (0.2 milli mol) of 7-(N$^\alpha$-t-butyloxycarbonyl-$\gamma$-benzyl-L-glutamyl-N$^\epsilon$-carbobenzoxy-L-lysyl-N$^\epsilon$-carbobenzoxy-L-lysyl)-amino-4-methylcoumarin was dissolved in 10 ml of methyl alcohol, 5 ml of acetic acid and 1 ml of water and added with 20 mg of a 5% palladium-carbon catalyst. The resulting mixture was stirred for 3 hours at room temperature and atmospheric pressure under circulation of hydrogen. The catalyst was then removed and the filtrate was subjected to concentration to a solid substance.

The residual product was refined by a column chromatography using "LH-20 gel" manufactured by Pharmacia Inc. (solvent, acetic acid of a 1 molarity; column size, 3.4 cm by 135 cm). The main fractions were collected and subjected to concentration and solid substance which was then dissolved in 10 ml of water and freeze dried to 7-(N$^\alpha$-t-butyloxycarbonyl-L-glutamyl-L-lysyl-L-lysyl)-amino-4-methylcoumarin.

Yield: 110 mg (65%); melting point, 140° C. (decomposition); specific rotation $[\alpha]_D^{27} = -65.0°$(C=1.08, H$_2$O).

Elementary analysis: Found: C 50.92%; H 6.97%; N 9.88%. Calculated as $C_{32}H_{48}N_6O_9 \cdot 2CH_3COOH \cdot 4 H_2O$: C 50.69%; H 7.57%; N 9.86%.

EXAMPLE 15

234 mg (0.2 milli mol) of 7-N$^\alpha$-t-butyloxycarbonyl-L-phenylalanyl-$\gamma$-benzyl-L-glutamyl-N$^\epsilon$-carbobenzoxy-L-lysyl-N$^\epsilon$-carbobenzoxy-L-lysyl)-amino-4-methylcoumarin was dissolved in 10 ml of methyl alcohol, 5 ml of acetic acid and 1 ml of water and added with 20 mg of a 5% palladium-carbon catalyst. The resulting mixture was stirred for 3 hours at room temperature and atmospheric pressure under circulation of hydrogen. The catalyst was then filtered off and the filtrate was subjected to concentration to a solid substance. The residual product was refined by column chromatography by using LH-20 gel manufactured by Pharmacia Inc. (solvent system, acetic acid of 1 molarity; column size, 3.4 cm by 135 cm) and the main fractions were collected and subjected to concentration to a solid substance. The latter was then dissolved in 10 ml of water and freeze dried to 7-(N$^\alpha$-t-butyloxycarbonyl-L-phenylalanyl-L-glutamyl-L-lysyl-L-lysyl)-amino-4-methylcoumarin.

Yield: 120 mg (61%); melting point, 160° C. (decomposition); specific rotation $[\alpha]_D^{27} = -49.2°$ (C=3.31, H$_2$O).

Elementary analysis: Found: C 55.30%; H 7.06%; N 9.99%. Calculated as $C_{41}H_{57}N_7O_{10} \cdot 2CH_3COOH \cdot 3H_3O$: C 55.03%; H 7.29%; N 9.99%.

Next, an experiment was conducted for demonstrating that the peptide derivative of the present invention may be used as a fluorescent substrate for enzymes.

0.1 to 0.2 milli mol of the substrate was dissolved in a mixture of 5 ml of dimethylsulfoxide and 5 ml of water and the resultant solution was diluted as a whole to 500 ml, by using a buffer solution (0.05 M tris- hydrochloric acid, pH 8.0, containing 0.1 M NaCl and 10 mM CaCl$_2$), for preparing substrate solutions.

2 ml of each substrate solution was introduced into a test tube and allowed to stand at 37° C. for 5 minutes. Then, 20 µl of the respective enzyme solutions was added to each test tube. After each test tube was shaken for 20 minutes at 37° C., 0.5 ml of 100% acetic acid was added into each test tube for terminating the reaction. For each sample thus obtained, increase in fluorescence was measured by using a wavelength of Em460 mm of the fluorescent spectrum (excited at 380 nm) for obtaining the degree of hydrolysis. The results are shown in the Table below.

| Substrate | Tripsin (µ moles/min/ mg protein) | Plasmin (µ moles/min/ mg protein) |
| --- | --- | --- |
| Boc-Phe-Glu-Lys-MCA . 2AcOH . H$_2$O | 7 | 0.12 |
| BOC-Ile-Glu-Lys-MCA . 2AcOH . H$_2$O | 12 | 0.11 |
| Boc-Glu-Lys-MCA . 2AcOH . H$_2$O | 0 | 0 |
| Boc-Phe-Glu-Lys-Lys-MCA . 2AcOH . 3H$_2$O | 2 | 0.23 |
| Boc-Glu-Lys-Lys-MCA . 2AcOH . 4H$_2$O | 146 | 0.57 |
| Boc-Val-Ley-Lys-MCA . 2AcOH . 2H$_2$O | 6 | 0.54 |

What is claimed is:

1. A peptide derivative having the formula

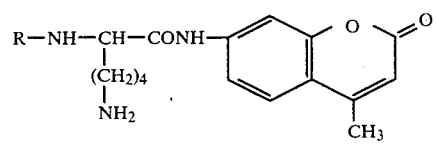

wherein R is a radical selected from the group consisting of hydrogen, glutamyl, isoleucyl-glutamyl, phenylalanyl-glutamyl, lysyl, glutamyl-lysyl, phenylalanyl-glutamyl-lysyl, leucyl, and valyl-leucyl.

2. The peptide derivative as claimed in claim 1 wherein the peptide derivative is in the form of an acid salt.

3. The peptide derivative as claimed in claim 1 wherein the $N^\alpha$-amino group is protected.

4. The peptide derivative as claimed in claim 1 wherein at least one of the $N^\epsilon$-amino groups is protected.

5. The peptide derivative as claimed in claim 1 wherein $\gamma$-carboxyl group is protected when glutamic acid constitutes a molecule.

6. The peptide derivative as claimed in claim 3 or 4 wherein the protective group for the amino group is the group selected from the group consisting of acyl, carbobenzoxy, tert-alkyloxycarbonyl, tosyl, and glutaryl.

* * * * *